United States Patent
Espinosa

(10) Patent No.: US 8,499,421 B2
(45) Date of Patent: Aug. 6, 2013

(54) RESTRAINING DEVICE

(76) Inventor: Edward Espinosa, Orange, CA (US)

(*) Notice: Subject to any disclaimer, the term of this patent is extended or adjusted under 35 U.S.C. 154(b) by 296 days.

(21) Appl. No.: 12/815,708

(22) Filed: Jun. 15, 2010

(65) Prior Publication Data

US 2010/0319412 A1    Dec. 23, 2010

Related U.S. Application Data

(60) Provisional application No. 61/218,196, filed on Jun. 18, 2009.

(51) Int. Cl.
*A61F 5/37* (2006.01)

(52) U.S. Cl.
USPC .................. 24/302; 70/16; 297/466

(58) Field of Classification Search
USPC ............ 24/302, 165, 300, 301, 298; 224/660, 224/666, 684; 70/16; 128/882, 876; 297/466
See application file for complete search history.

(56) References Cited

U.S. PATENT DOCUMENTS

| | | | | | |
|---|---|---|---|---|---|
| 1,903,081 | A | * | 3/1933 | Wotherspoon | 224/223 |
| 4,004,583 | A | * | 1/1977 | Johnson | 297/468 |
| 4,422,455 | A | * | 12/1983 | Olsen | 128/878 |
| 4,728,553 | A | * | 3/1988 | Daniels | 428/100 |
| 4,784,889 | A | * | 11/1988 | Daniels | 428/100 |
| 4,949,679 | A | * | 8/1990 | Wolfer | 70/16 |
| 5,075,932 | A | * | 12/1991 | Hunt et al. | 24/16 PB |
| 5,469,813 | A | * | 11/1995 | Peden | 119/770 |
| 5,581,853 | A | * | 12/1996 | Miller et al. | 24/302 |
| 6,138,677 | A | * | 10/2000 | DeVane | 128/869 |
| 6,418,594 | B1 | * | 7/2002 | Miller | 24/298 |
| 7,223,212 | B2 | * | 5/2007 | DiOrio et al. | 482/83 |
| 2003/0097736 | A1 | * | 5/2003 | Blankenship | 24/302 |
| 2004/0262353 | A1 | * | 12/2004 | Lambert | 224/578 |
| 2007/0062012 | A1 | * | 3/2007 | Caison | 24/302 |
| 2007/0205235 | A1 | * | 9/2007 | Knight et al. | 224/223 |
| 2009/0095232 | A1 | * | 4/2009 | McKay | 119/770 |
| 2011/0067953 | A1 | * | 3/2011 | Kopp | 182/3 |

* cited by examiner

*Primary Examiner* — Robert J Sandy
*Assistant Examiner* — Rowland D Do
(74) *Attorney, Agent, or Firm* — Loza & Loza LLP; Heidi L. Eisenhut

(57) ABSTRACT

A restraining device for restricting mobility an individual is provided. The restraining device includes an elongated strap having first and second ends. An attaching member, having first and second portions, is secured to the elongated strap, where the first portion is attached to the first end and the second portion is slidably attached to the second end creating a retaining loop for tightly wrapping around an individual's legs. The second end of the elongated strap is extended out a car door leaving the second end hanging outside the car. A retaining strap, defining a series of loops, is attached to a side of the second end of the elongated strap between the second portion of the attaching member and a ring which is attached to the second end of the elongated strap. A fastening member is attached to the ring and is used to adjust the length of the second end hanging outside the car.

17 Claims, 5 Drawing Sheets

RESTRAINING DEVICE

CLAIM OF PRIORITY UNDER 35 U.S.C. §119

The present Utility Application for patent claims priority to U.S. Provisional Application No. 61/218,196 entitled "Restraining Device" filed Jun. 18, 2009, and hereby expressly incorporated by reference herein.

FIELD OF INVENTION

At least one feature pertains to physical restraints.

BACKGROUND OF INVENTION

When an individual is arrested, handcuffs are used to secure the individual's wrists close together so that he/she cannot move their wrists more than a few centimeters/inches apart making many tasks difficult or impossible. This is usually done to prevent suspected criminals from escaping police custody and harming themselves or others. Once handcuffed, the suspect is placed in the back seat of a squad car and transported to jail.

Although the suspect has been handcuffed, transporting the suspect to jail is dangerous can have very tragic consequences. Even though handcuffed, unruly prisoners have a considerable ability to move around. They can position themselves so as to slam their feet against doors and windows, often causing damage to the car's interior. Particularly physical prisoners have been known to break out windows, for example. When prisoners exhibit such extreme behavior, the end results can be dangerous. In addition to damaging the squad car, they also pose a danger to police officers being injured or killed, prisoners escaping, endangering the public, bad press, and unneeded job stress for the police officer.

To reduce the above mentioned problems and dangers, shackles or chains have been used to restrain the legs and feet of a prisoner once a prisoner has been subdued, but such leg manacles cannot be readily placed on the prisoner and are not practical for use by an arresting officer. Moreover, unless heavily weighted, they would not prevent the prisoner from lashing out with his or her feet.

Consequently, what is needed is a restraining device which is light weight, can be easily carried on belts of the police officers and which alleviates the problems and dangers inherent in transporting suspects as described previously.

SUMMARY

In one aspect, a restraining device for restricting the range of motion and mobility of the legs of an individual is provided. The restraining device may include an elongated strap having a first end and a second end. An attaching member having a first portion and a second portion may be secured to the elongated strap, where the first portion may be attached to the first end of the elongated strap and the second portion may be slidably attached to the second end of the elongated strap creating a retaining loop for wrapping around the legs of the individual. Once wrapped around the legs, the second portion may slide freely on the elongated strap adjusting the size of the retaining loop so that the retaining loop may be drawn tightly around the legs.

Once secured to the legs, the individual may be placed in a car and the second end of the elongated strap is extended out of the car and the car door is closed over the second end of the elongated strap leaving a portion of the second end hanging outside the car. A retaining strap may be attached to at least one side of the second end of the elongated strap between the second portion of the attaching member and a ring which is attached to the second end of the elongated strap. The retaining strap may define a series of loops across a section of the elongated strap. A fastening member may be attached to the ring and used to adjust the length of the second end of the elongated strap hanging outside of the car.

To prevent the second end of the elongated strap from dragging on the ground, or from being entangled with the tire or an object on the road, the length of the second end of the elongated strap may be adjusted. To adjust the length of the second end, the elongated strap is folded back towards the car shortening the length. As the ring is secured/lodged against the car door, it may be prevented from being pulled into the interior of the car thus restricting the range of motion and mobility of the individual's legs inside the car.

To release the restraining device, the ring may be released from the loop freeing the second end of the elongated strap. Then the car door may be opened and the individual taken out of the car and the second portion of the attaching member may be detached from the first portion of the attaching member. As a result, the legs of the individual are no longer restrained. Alternatively, the restraining device may be removed prior to the suspect being taken out of the car.

In another aspect, the restraining device may be compactly folded so that it may fit into a pouch attached to an Officer's belt. As the restraining device is light weight and compact, it may easily be carried by officers on patrol.

BRIEF DESCRIPTION OF THE DRAWINGS

The features, nature, and advantages of the present aspects may become more apparent from the detailed description set forth below when taken in conjunction with the drawings in which like reference characters identify correspondingly throughout.

DETAILED DESCRIPTION

The following detailed description is of the best currently contemplated modes of carrying out the invention. The description is not to be taken in a limiting sense, but is made merely for the purpose of illustrating the general principles of the invention.

In the following description, certain terminology is used to describe certain features of one or more embodiments of the invention. The term "attaching member" refers to a hook; clasp or any other type of device that may be used for attaching items together. The term "suspect" refers to any individual being detained. The term "fastening member" refers to a ring-hook, clamp or any other time of device that may be used for securing or attaching items together.

Figure 1:
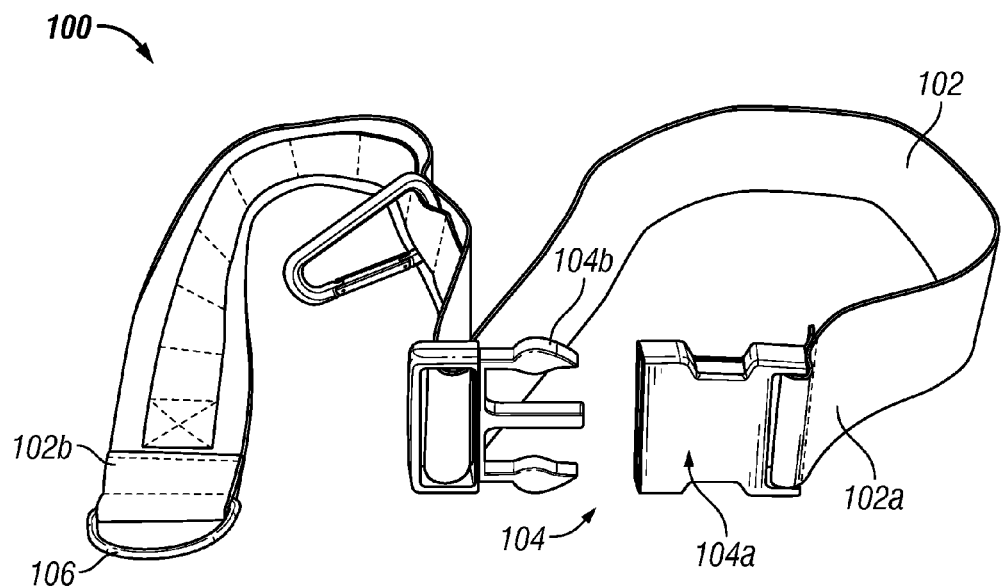
FIG. 1 illustrates a perspective view of a restraining device, according to an embodiment of the invention, in an unfolded, unbuckled configuration.

FIG. 1 illustrates a perspective view of a restraining device, according to an embodiment of the invention, in an unfolded, unbuckled configuration. As shown, the restraining device 100 may include an elongated strap 102 having a connector or attaching member 104. The attaching member 104 may include a first portion 104a and a second portion 104b. In one aspect, the first portion may be a female portion and the second portion may be a male portion.

In securing the elongated strap 102 to the female portion 104a, a first end 102a of the elongated strap 102 may pass, in a known manner, through an opening in the female portion 104a and may then be reverse folded, or doubled-back on itself, and sewn together to secure attachment to the female portion 104a. In securing the elongated strap 102 to the male portion 104b, a second end 102b of the elongated strap may be extended through an opening in the male portion 104b allowing the male portion 104b to slide freely on the elongated strap 102. The female portion 102a and the male portion 102b may be detachably connected together creating a retaining loop 108. (See FIG. 2) As the male portion 104b may slide freely on the elongated strap 102, the size of the retaining loop 108 may be adjustable allowing the retaining loop 108 to be drawn tightly around the ankles or legs of an individual or suspect (hereinafter used interchangeably).

The second end 102b of the elongated strap 102 may include a ring 106, such as a D-ring, for attaching one or more ring-hooks 110. (see FIG. 2) As described in detail below, the ring-hooks 110 may be used to prevent the elongated strap 102 from dragging on the ground.

A retaining strap 111 may be secured to one or both sides of the elongated strap 102 at pre-defined distances defining a series of loops 116 across the elongated strap 102. In one embodiment, the retaining strap 111 may be secured to the elongated strap 102 between the ring 106 and the male portion 104a of the attaching member 104.

The retaining strap 111 may be secured to the elongated strap 102 by any means known in the art, including, but not limited to, sewing the ends, and pre-defined distances in between the ends, of the retaining strap 111 to the second end 102b of the elongated strap 102. In an alternative embodiment, a series of individual retaining straps may be secured to the elongated strap creating the series of loops 116. As described in detail below, the series of loops 116 may be used to adjust the length of the second end 102b of the elongated strap hanging outside of a car.

Figure 2:
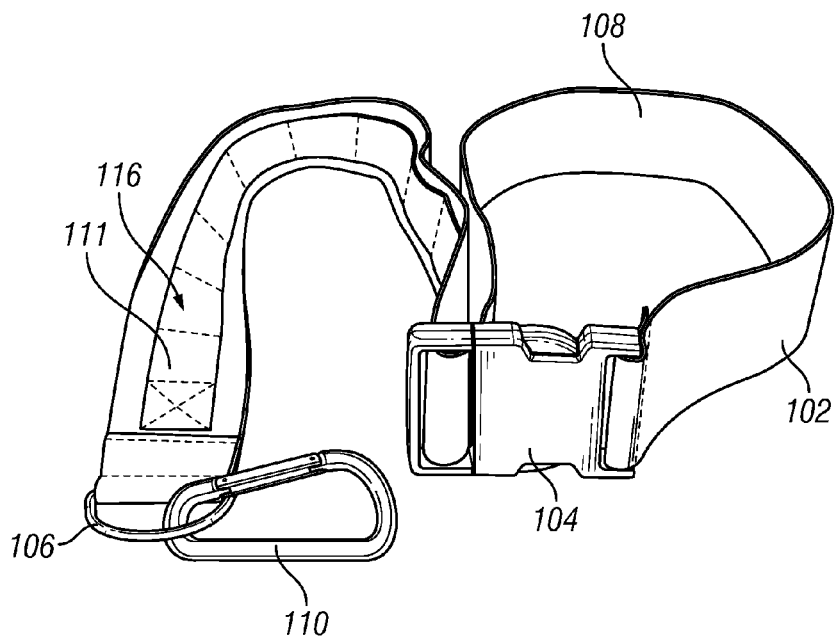
FIG. 2 illustrates a perspective view of a restraining device, according to an embodiment of the invention, in an unfolded, buckled configuration.

FIG. 2 illustrates a perspective view of the restraining device of FIG. 1 in an unfolded, buckled configuration. To utilize the restraining device 100 of the present invention, the wrists of a suspect may first be secured with handcuffs, flex-cuffs, or any other known device for binding wrists together. Once the wrists are secured, a police officer may then place the restraining device 100 around the feet or ankles of the suspect. When using the restraining device 100, the police officer may release/separate the male portion 104a from the female portion 104b of the attaching member 104 and place or encircle the elongated strap 102 about the ankles or legs of the suspect such that the ankles or legs are within the retaining loop 108. The restraining device 100 may be placed onto the suspect prior to or as he is placed into the back seat of a squad car 114. (See FIG. 4)

As described above, when the suspect is under arrest and placed into the squad car 114, if the legs (or ankles) 112 of the suspect are not restrained, the suspect may use his legs 112 to kick or push his feet against doors and windows of the squad car 114 which can result in damage to the car, such as a broken window. When a squad car is damaged, it is taken out of service for repair resulting in fewer officers patrolling the street which may pose an increased danger to the public. Furthermore, suspects exhibiting such extreme behavior can have other dangerous results. In addition to damaging the squad car 114, they also pose a danger to police officers being injured or killed, escaping, endangering the public, bad press, and unneeded job stress.

Figure 3:
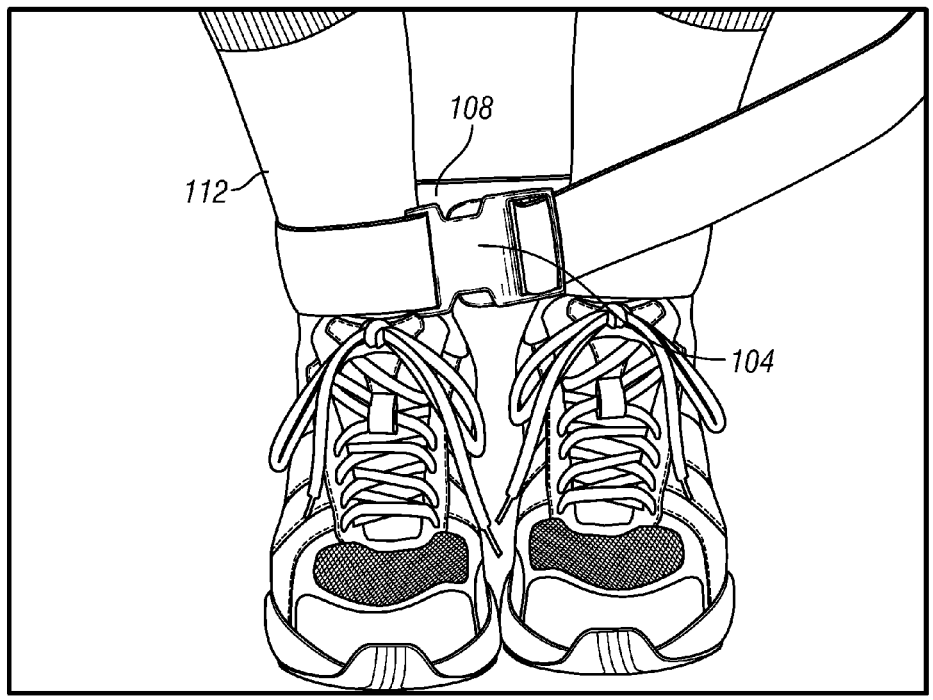
FIG. 3 illustrates the restraining device of FIG. 1 secured to the ankles of an individual.
Figure 4:
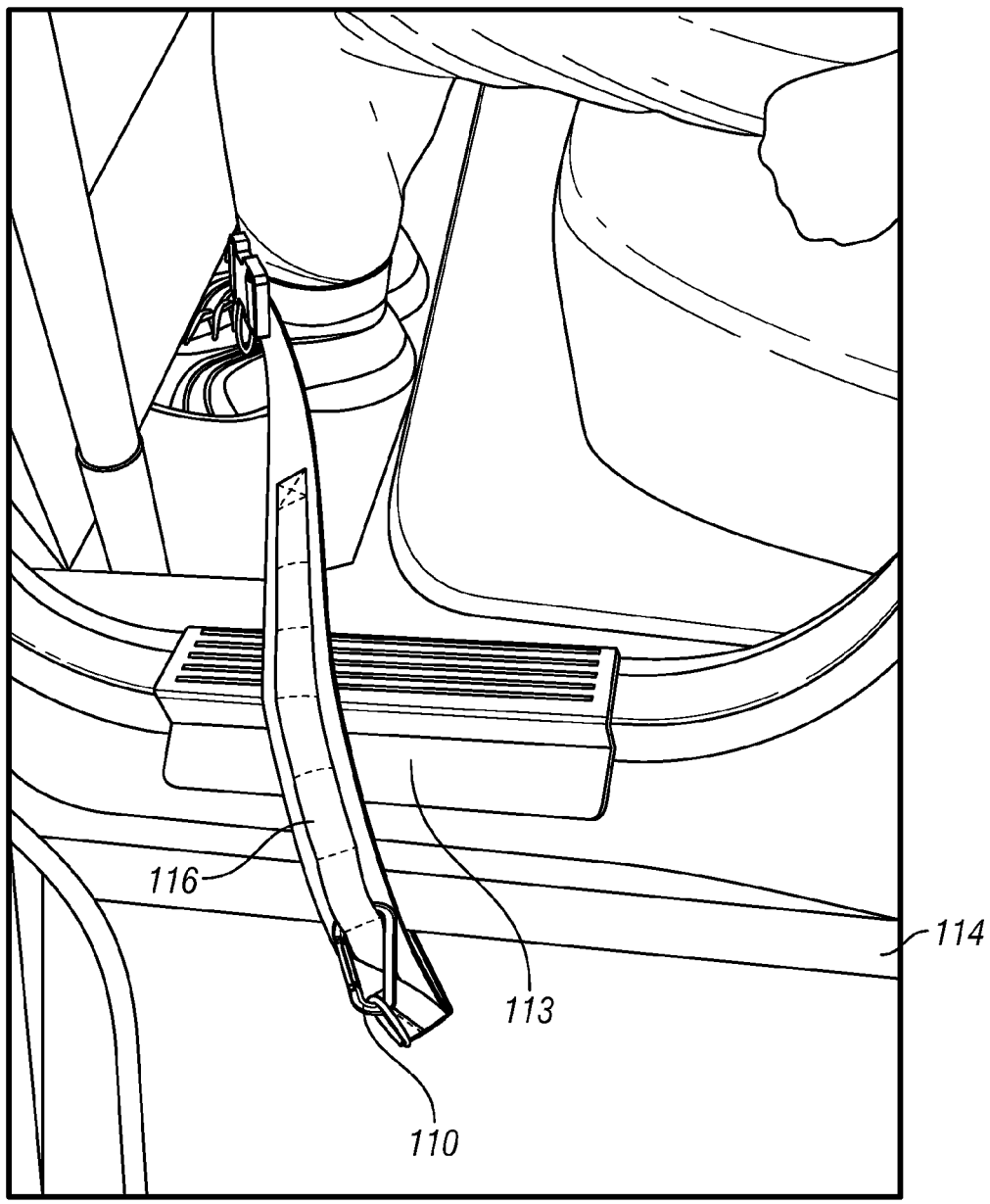
FIG. 4 illustrates the restraining device of FIG. 1 secured to the ankles of an individual and extending out of a car.

FIGS. 3-4 illustrate the restraining device 100 of FIG. 1 secured to the ankles of an individual. Once placed/encircled around the ankles or legs 112 of the suspect, the male portion 104b of the attaching member 104 may be inserted into the female portion 104a of the attaching member 104 forming the retaining loop 108. The retaining loop 108 may then be tightened around the ankles or legs 112 of the suspect by pulling on the second end 102b of the elongated strap 102 through the opening in the male portion 104b of the attaching member 104.

Figure 5:
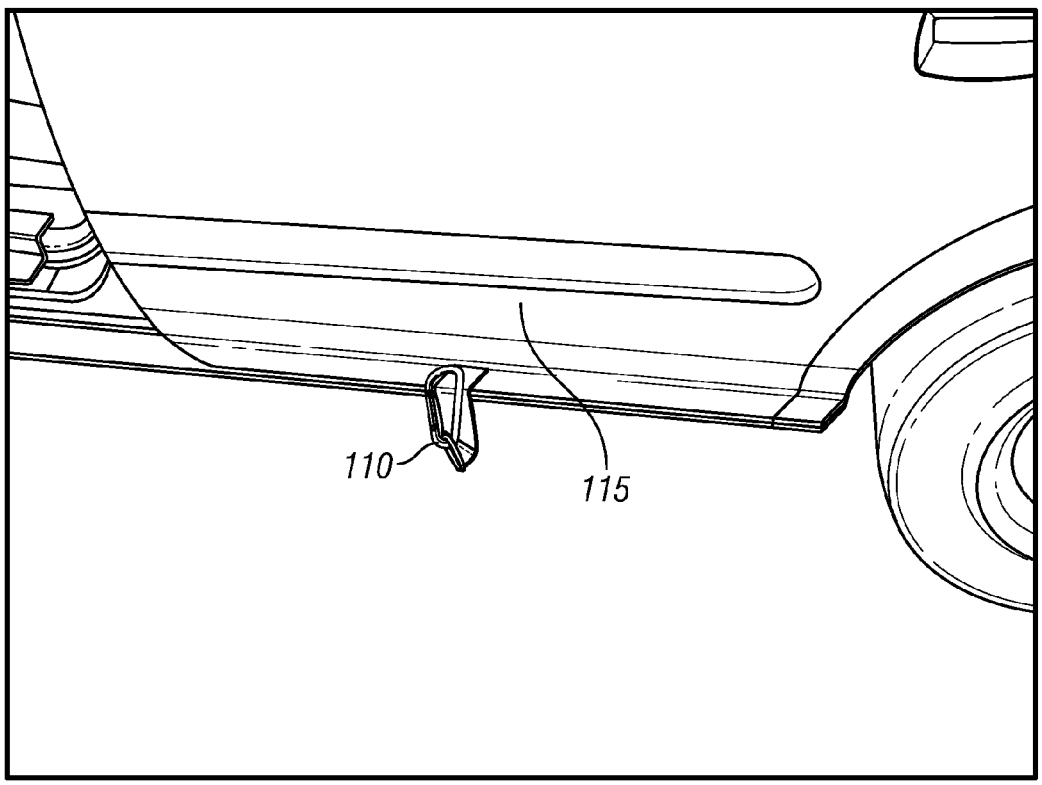
FIG. 5 illustrates the restraining device of FIG. 1 extended out a closed car door.

After the retaining loop 108 has been tightened around the suspect's ankles or legs 112, the suspect may be placed in the back seat of a squad car 114. Alternatively, the restraining device 100 may be placed on the suspect once he has been put into the back of the car. The second end 102b of the elongated strap 102 may then be extended out of the car (see FIGS. 4-5) and the car door 115 may then be closed on the second end 102b of the elongated strap 102 leaving the second end 102b of the elongated strap 102 hanging outside the car 114. That is, the second end 102b of the elongated strap 102 may be secured to the car by the bottom of the car door 115.

To prevent the second end 102b of the elongated strap 102 from dragging on the ground, or from being entangled with the tire or an object on the road, the length of the second end 102b of the elongated strap 102 may be adjusted. To adjust the length of the second end 104b, the hook-ring 110 may be secured to the D-ring 106 and to a loop in the series of loops 116 located on one or both sides of the elongated strap 102. When the hook-ring 110 is secured to both the D-ring 106 and to a loop in the series of loops 116, the elongated strap 102 is folded back towards the car shortening the length (see FIG. 5). As each loop is a different distance away from the ring-hook, the length of the strap may be adjusted based upon which loop the ring-hook is secured to. The closer the loop is to the male portion 104b of the attaching member 104 the shorter the length. Conversely, the farther the loop is from the male portion 104b of the attaching member, the longer the length. Consequently, the larger the size of the legs of the suspect, the shorter the second end 102b of the elongated strap 102 hanging out of the car. Conversely, the smaller the size of the legs of the suspect, the longer the second end 102b of the elongated strip 102 hanging out of the car.

As the ring-hook can only be pulled toward the car door by the suspect, once it is secured/lodged against the car door 115 (see FIG. 5), it may be prevented from being pulled into the interior of the car thus restricting the range of motion and mobility of the suspect's feet inside the car.

To release the restraining device 100 from the suspect, the D-ring 106 may be released from the loop in the series of loops 116, thereby freeing the second end 102b of the elongated strap 102. Then the car door may be opened and the suspect taken out. Once the suspect is out of the car, the male portion 104a of the attaching member 104 may be detached from the female portion 104b of the attaching member 104. In an alternative embodiment, the restraining device 100 may be removed prior to the suspect being taken out of the car.

Figure 6:
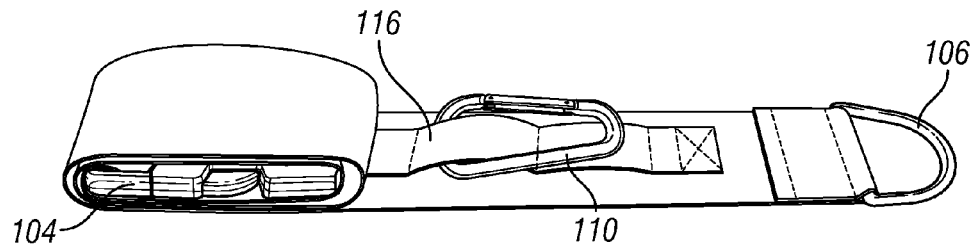
FIG. 6 illustrates the restraining device of FIG. 1 in a partially folded, buckled configuration.
Figure 7:
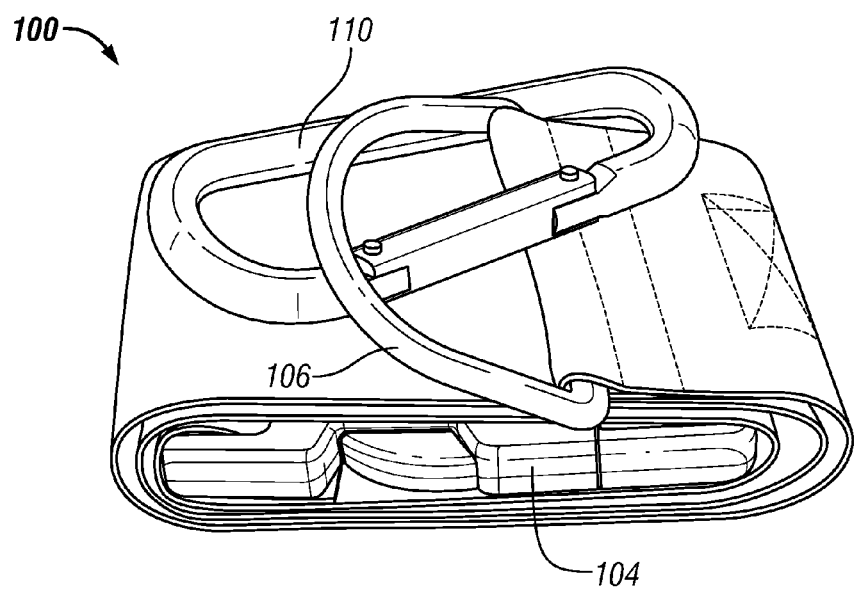
FIG. 7 illustrates the restraining device of FIG. 1 in a folded, buckled configuration.

As shown in FIGS. 6-7, the restraining device 100 may be compactly folded so that it may fit into a pouch attached to an Officer's belt. As the restraining device 100 is light weight and compact, it may easily be carried by officers on patrol.

In addition to restraining an individual's legs, the restraining device 100 of the present invention may have additional uses including, but not limited to, restraining other body parts of an individual and as a tourniquet.

One or more of the components and functions illustrated in FIGS. 1, 2, 3, 4, 5, 6 and/or 7 may be rearranged and/or combined into a single component or embodied in several components without departing from the invention. Additional elements or components may also be added without departing from the invention.

While certain exemplary embodiments have been described and shown in the accompanying drawings, it is to be understood that such embodiments are merely illustrative of and not restrictive on the broad invention, and that this invention is not be limited to the specific constructions and arrangements shown and described, since various other modifications may occur to those ordinarily skilled in the art.

What is claimed is:

1. A restraining device, comprising:
   an elongated strap having a first end and a second end;
   an attaching member having a first portion and a second portion, the first portion attached to the first end of the elongated strap where the first end of the elongated strap extends through an opening in the attachment member, is reverse folded and sewn together securing the first end of the elongated strap to the attachment member, and the second portion having an opening through which the second end of the elongated strap is slidably received;
   a ring attached to the second end of the elongated strap where the second end of the elongated strap extends through the ring, is reverse folded and sewn together securing the second end of the elongated strap to the ring;
   a retaining strap attached to a side of the elongated strap between, and separate from, the reverse folded second end of the attachment strap and the second portion of the attaching member, the retaining strap defining a series of loops across a section of the elongated strap, wherein each loop in the series of loops having a first side fixedly secured to the elongated strap and a second side fixedly secured to the elongated strap, and wherein the each loop in the series of loops shares at least one of the first side and the second side of an adjacent loop in the series of loops; and
   a fastening member attached to the ring wherein the fastening member hooks onto a loop in the series of loops to adjust the length of the second end and prevent the second end from dragging on the ground outside the car.

2. The restraining device of claim 1, wherein the first portion is female and the second portion is male.

3. The restraining device of claim 1, wherein the elongated strap is adapted for placement around ankles of an individual and the first portion of the attaching member is connected to the second portion of the attaching member creating a retaining loop.

4. The restraining device of claim 3, wherein the retaining loop may be tightened by pulling the second end of the elongated strap through the second portion.

5. The restraining device of claim 1, wherein the second end of the elongated strap is extended out of a car and a door on the car is closed over the second end of the elongated strap leaving the second end hanging outside the car.

6. The restraining device of claim 1, wherein the ring is a D-ring.

7. The restraining device of claim 1, wherein the fastening member is a ring-hook.

8. The restraining device of claim 1, wherein the fastening member prevents the second end of the elongated strap from being pulled into the car and restricts mobility of the individual.

9. The restraining device of claim 1, wherein the each loop in the series of loops has an upper end and a lower end, the upper end and the lower end unattached to the elongated strap and integrally connected to the first and second sides of the each loop in the series of loops.

10. The restraining device of claim 1, wherein the elongated strap has a first width and the retaining strap has a second width, and wherein the first width is greater than the second width.

11. The restraining device of claim 1, wherein the elongated strap and the retaining strap are formed from separate strips of material.

12. A restraining device, comprising:
    an elongated strap having a first end and a second end;
    an attaching member having a first portion and a second portion, the first portion attached to the first end of the elongated strap where the first end of the elongated strap extends through an opening in the attachment member, is reverse folded and sewn together securing the first end of the elongated strap to the attachment member, and the second portion having an opening through which the second end of the elongated strap slidably received, where the elongated strap is adapted for placement around legs of an individual and the first portion is connected to the second portion creating a retaining loop;
    a ring attached to the second end of the elongated strap where the second end of the elongated strap extends through the ring, is reverse folded and sewn together securing the second end of the elongated strap to the ring;
    a retaining strap attached to a side of the elongated strap between, and separate from, the reverse folded second end of the attachment strap and the second portion of the attaching member, the retaining strap defining a series of loops across a section of the elongated strap, wherein each loop in the series of loops having a first side fixedly secured to the elongated strap and a second side fixedly secured to the elongated strap, and wherein the each loop in the series of loops shares at least one of the first side and the second side of an adjacent loop in the series of loops; and
    a fastening member attached to the ring wherein the fastening member hooks onto a loop in the series of loops to adjust the length of the second end and prevent the second end from dragging on the ground outside the car;
    wherein the elongated strap has a first width and the retaining strap has a second width, and wherein the first width is greater than the second width; and
    wherein the elongated strap and the retaining strap are formed from different strips of material.

13. The restraining device of claim 12, wherein the retaining loop is adapted for tightening around the legs of the individual immobilizing the legs.

14. The restraining device of claim 13, wherein the retaining loop is tightened by pulling the second end of the elongated strap through an opening in the second portion of the attaching member.

15. The restraining device of claim 14, wherein the second end of the elongated strap extends out of a car and a door on the car is closed over the second end of the elongated strap leaving the second end hanging outside the car.

16. The restraining device of claim 12, wherein the fastening member remains outside the car and is adapted to restrict range of motion and mobility of the legs of the individual inside the car when the door is closed over the second end of the elongated strap.

17. The restraining device of claim 12, wherein the first portion is female and the second portion is male.

* * * * *